United States Patent [19]

Kvita et al.

[11] 4,250,096
[45] Feb. 10, 1981

[54] 3- AND 4-AZIDOPHTHALIC ACID DERIVATIVES

[75] Inventors: Vratislav Kvita, Muttenz; Hans Zweifel, Basel, both of Switzerland; Gerd Greber, Bad Vöslau, Austria

[73] Assignee: Ciba-Geigy Corporation, Ardsley, N.Y.

[21] Appl. No.: 948,857

[22] Filed: Oct. 5, 1978

[30] Foreign Application Priority Data

Oct. 14, 1977 [CH] Switzerland ............ 12577/77

[51] Int. Cl.³ .................................. C07D 209/48
[52] U.S. Cl. .................... 260/326 N; 260/326 S; 260/349; 430/270; 430/313; 525/327; 525/329; 525/375
[58] Field of Search ................... 260/326 N, 326 S

[56] References Cited

U.S. PATENT DOCUMENTS

| | | | |
|---|---|---|---|
| 3,002,003 | 1/1961 | Merrill et al. | 260/346.3 |
| 3,712,814 | 1/1973 | Ranz et al. | 96/36 |
| 3,804,852 | 4/1974 | Haemmerle et al. | 260/326 C |
| 3,878,224 | 4/1975 | Matsui et al. | 260/326 N |

FOREIGN PATENT DOCUMENTS

| | | |
|---|---|---|
| 49-023843 | 6/1974 | Japan . |
| 678599 | 9/1952 | United Kingdom . |
| 843541 | 8/1960 | United Kingdom . |
| 928039 | 6/1963 | United Kingdom . |

OTHER PUBLICATIONS

R. Steele et al., Chem. Abstr., 82: 31878q, (1975).
K. Kato, et al., Chem. Abstr., 78: 124224f, (1973).
B. Vollmert et al., Chem. Abstr., 67: 117709n, (1967).
S. Merrill et al., J. Appl. Polymer Sci., 7, pp. 273–279, (1963), Photosensitive Azide Polymers.
S. Marburg et al., Tetrahedron Letters, 12, 1305, (1966).

*Primary Examiner*—Jose Tovar
*Assistant Examiner*—M. C. Eakin
*Attorney, Agent, or Firm*—Luther A. R. Hall

[57] ABSTRACT

The compounds according to the invention have the formulae Ia or Ib

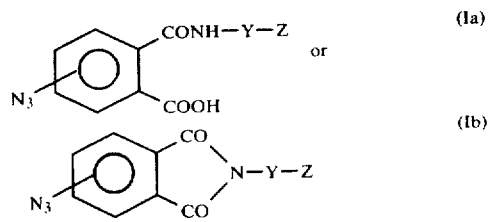

in which Y is a divalent organic radical and Z is —NH₂, —NH-alkyl having 1–4 C atoms, —OH, —COOH, —COCl, —O—CO—CH=CH₂,

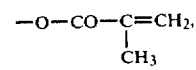

—COO—CH=CH₂ or —O—CH=CH₂.

These novel 3- or 4-azidophthalic acid derivatives may be used for the preparation of photo-crosslinkable polymers. Compared to corresponding photosensitive polymers of the prior art, these novel polymers have the advantages that they are even more photosensitive and that they also absorb in the long wavelength UV region (at wavelengths greater than 320 nm).

5 Claims, No Drawings

3- AND 4-AZIDOPHTHALIC ACID DERIVATIVES

The present invention relates to novel 3- or 4-azidophthalic acid derivatives and to processes for their preparation. The 3- and 4-azidophthalic acid derivatives according to the invention can be used to produce photocurable polymers.

The literature discloses that polymers having azido side groups can be photo-crosslinked and are suitable for photo-mechanical applications [cf., for example, British Patent Specification No. 843,541, U.S. Pat. No. 3,002,003, Journal of Appl. Poly. Sci., 7, 273–279 (1963) and Japanese Laid-Open Specification 74/23843]. These prior-art polymers have disadvantages inasmuch as they absorb predominantly in the short wavelength UV region and are therefore unsuitable, or rather unsuitable, for numerous applications, especially in the field of micro-electronics, which demand highly photosensitive substances which absorb in the longer wavelength UV region.

It was therefore the object of the invention to provide novel substances which are suitable for the preparation of polymers which have increased photosensitivity and absorb in the longer wavelength UV region (above 320 nm).

The novel 3- and 4-azidophthalic acid derivatives have the formula Ia or Ib

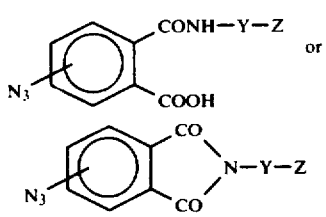

in which Y is unsubstituted or substituted alkylene having 2–18 C atoms, an unsubstituted or substituted phenylene, naphthylene, biphenylene, cyclohexylene or dicyclohexylmethane group or an unsubstituted or substituted

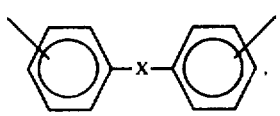

group, X is —O—, —S—, —SO$_2$—,

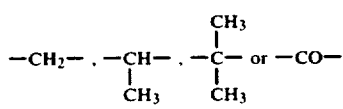

and Z is —NH$_2$, —NH-alkyl having 1–4 C atoms, —OH, —COOH, —COCl, —O—CO—CH=CH$_2$,

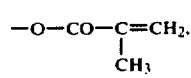

—COO—CH=CH$_2$ or —O—CH=CH$_2$.

Alkylene groups Y may be straight-chain or branched and can be substituted, for example by one or more phenyl groups, cycloalkyl groups having 5–8 C atoms or aralkyl groups having 7 or 8 C atoms. Preferred substituted alkylene groups Y are those which are substituted by one or two phenyl groups or by one or two cycloalkyl or aralkyl groups according to the definition given, such as the cyclohexyl or benzyl group.

Examples of such alkylene groups Y are the 1,2-ethylene, 1,3- or 1,2-propylene, 1,4- or 1,3-butylene, pentamethylene, hexamethylene, 2-methyl-4-dimethylhexamethylene, 2-dimethyl-4-methylhexamethylene, 1,10-dicyclohexyl- or 1,10-dicyclooctyl-decamethylene, 1,10-diisopropyldecamethylene, 1,1,10,10-tetramethyldecamethylene, 1,10-diethyl-1,10-dimethyldecamethylene, octamethylene, decamethylene, dodecamethylene and 1-ethyl-10,10-dimethylundecamethylene. Unsubstituted straight-chain or branched alkylene groups, especially those having 2–16 C atoms, are preferred.

Phenylene, naphthylene, diphenylene, cyclohexylene or dicyclohexylmethane groups Y, or

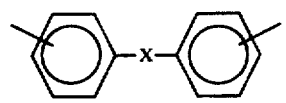

groups Y, can also be substituted, for example by halogen atoms, such as fluorine, chlorine or bromine, alkyl groups having 1–4 C atoms, especially methyl or ethyl, cycloalkyl groups having 5–7 C atoms, especially cyclopentyl and cyclohexyl, or aralkyl groups having 7 or 8 C atoms, such as benzyl or β-phenylethyl. The said groups can have several substituents of the type mentioned on each ring, but advantageously are substituted by only one of the said groups per ring, especially by chlorine or bromine, methyl or ethyl.

Preferably, however, phenylene, naphthylene, cyclohexylene, biphenylene, dicyclohexylmethane and

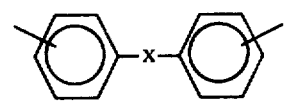

groups Y are unsubstituted, and advantageously X is —O—, —SO$_2$— or —CH$_2$—. Cyclohexylene, naphthylene and in particular phenylene groups are particularly preferred.

The N$_3$ group is preferably joined to the benzene ring in the ortho-position to the carboxyl or carboxamide group or to a carbonyl group.

Preferred compounds are those of the formula Ia, and especially those of the formula Ib, in which Y is unsubstituted straight-chain or branched alkylene and Z is as defined under formula Ia or Ib, but in particular compounds of the formula Ia, and especially compounds of the formula IB, in which Y is unsubstituted alkylene having 2–18, especially 2–16, C atoms, cyclohexylene, naphthylene or phenylene and Z is —NH$_2$, —COOH, —COCl, —OH, —O—CO—CH=CH$_2$ or

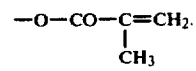

Particularly preferred products according to the invention are compounds of the formula VII

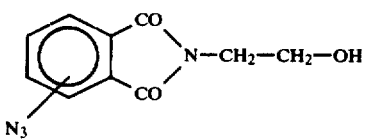

preferably N-(β-hydroxyethyl)-3-azidophthalimide, and compounds of the formula VIII

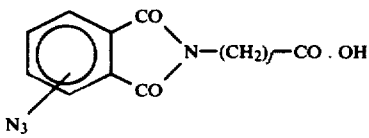

in which f is from 1 to 5, preferably 5, the preferred compound being 6-(3-azidophthalimidyl)-caproic acid, and compounds of the formula IX

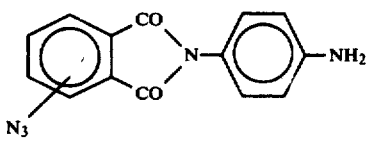

preferably 4-(3-azidophthalimidyl)-aniline, and compounds of the formula X

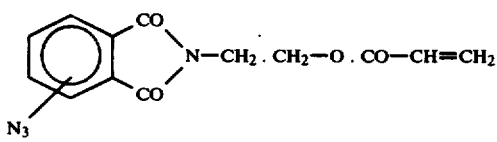

and compounds of the formula XI

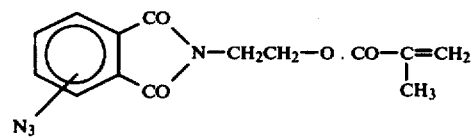

The compounds of the formula Ib can be prepared in a particularly advantageous manner by reacting a compound of the formula II

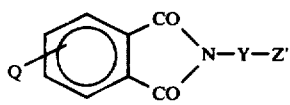

in which Y is defined as under formula Ib, Z' is a group corresponding to Z but is not —COCl and Q is a halogen atom, such as chlorine, bromine or fluorine, or is the nitro group, in an inert organic solvent, at a temperature between about 0° C. and 120° C., preferably between about 50° C. and 90° C., with an azide of the formula III $M^{n+} \, (N_3^-)_n$ (III)

in which n is 1 or 2 and M is an alkali metal cation, alkaline earth metal cation or quaternary ammonium cation, and if desired converting the resulting compound of the formula Ib, in which Z is —COOH, to the corresponding acid chloride by treatment with a suitable chlorinating agent, such as thionyl chloride, oxalyl chloride or phosgene.

the literature [Tetradedron Letters, 12, 1305–1309 (1966)] discloses that 3-nitrophthalic anhydride can be converted to 3-azidophthalic anhydride by means of sodium azide in the presence of an inert organic solvent at a temperature of 110° C. However, 4-nitrophthalic anhydride and 3-chlorophthalic anhydride cannot be converted to the corresponding azide by this method. It is therefore surprising that, according to the invention, both the 3-nitro- and 4-nitro-phthalimides of the formula II, and the corresponding 3- and 4-halogen compounds, can be converted to the corresponding azides and the reaction can furthermore in most cases be carried out at substantially lower temperatures, with good to very good yields. A prior expensive separation of the starting materials into the 3- and 4-isomers is therefore not necessary in the process according to the invention.

Preferably, Q is the nitro group. A quaternary ammonium cation M is, for example, a tetraalkylammonium cation or benzyltrialkylammonium cation, with each alkyl moiety having 1–12 and especially 1–4 C atoms, especially the tetramethylammonium cation and the trimethyl benzylammonium cation.

Examples of suitable alkali metal azides and alkaline earth metal azides are lithium, sodium, potassium, calcium, magnesium and barium azide. Alkali metal azides, above all sodium azide, are preferred. The azide is advantageously employed in excess, for example in a molar excess of about 5–50% and preferably of about 10–30%.

Examples of suitable inert organic solvents are polar solvents, for instance lower aliphatic alcohols, for example those having not more than 6 C atoms, such as methanol, ethanol, propanol, isopropanol, butanols and pentanols, dibenzyl ethers and dialkyl ethers with each alkyl moiety having 1–4 C atoms, such as diethyl ether, di-n-propyl ether and di-isopropyl ether, cyclic ethers, such as tetrahydrofuran, tetrahydropyran and dioxan, and diethylene glycol dialkyl ethers and triethylene glycol dialkyl ethers with each alkyl moiety having 1–4 C atoms, such as diethylene glycol diethyl ether and di-n-butyl ether, and triethylene glycol dimethyl ether.

It is advantageous to use aprotic polar solvents, such as aliphatic and aromatic nitriles, such as alkylnitriles having 2–5 C atoms in the alkyl moiety, for example acetonitrile, propionitrile and butyronitrile, or benzonitrile, cyclic amides, such as N-methyl-2-pyrrolidone, N-acetyl-2-pyrrolidone and N-methyl-ε-caprolactam, N,N-dialkylamides of aliphatic monocarboxylic acids having 1–3 C atoms in the acid moiety, such as N,N-dimethylformamide, N,N-dimethylacetamide, N,N-diethylacetamide and N,N-dimethylmethoxyacetamide, dialkylsulphoxides, such as dimethylsulphoxide and diethylsulphoxide hexamethylphosphoric acid triamide (hexametapol), and tetrahydrothiophene dioxide (sulpholan). Preferred solvents are dialkylsulphoxides, especially dimethylsulphoxide.

Compounds of the formula Ia and Ib, in which Z≠ —OCH=CH₂, can also be prepared by a modified method which comprises reacting a compound of the formula IV

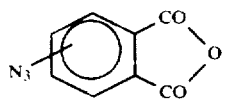

with an amine of the formula V

  (V)

to give a compound of the formula VI

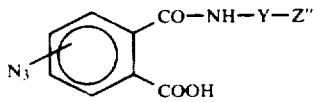  (VI), in which formulae Y is as defined under formula Ia or Ib and Z" is —NH$_2$, —NH-alkyl having 1–4 C atoms, —OH, —COOH, —O—CO—CH=CH$_2$,

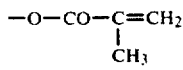

or —COO—CH=CH$_2$, thereafter, if appropriate, cyclising the compound of the formula VI and, if desired, converting compounds of the formula Ib, in which Z is —COOH, to the corresponding acid chloride by treatment with a chlorinating agent.

The reaction of the anhydride of the formula IV with the amine of the formula V is advantageously carried out in an organic medium, at temperatures between about 0° C. and 120° C., depending on the nature of the reactants. Advantageously, the anhydride of the formula IV is employed in stoichiometric amount, or in slight excess over the amine of the formula V, for example in an excess of up to about 20 mol %.

Examples of suitable organic solvents are aprotic solvents of the abovementioned type, as well as non-halogenated and halogenated aliphatic or aromatic hydrocarbons, such as methylene chloride, chloroform, carbon tetrachloride, 1,1,2-trichloroethane, 1,2-dichloroethane, benzene, toluene and chlorobenzene, and aliphatic and cycloaliphatic ketones, such as acetone, methyl ethyl ketone, cyclopentanone and cyclohexanone.

The cyclisation of the compounds of the formula VI can be carried out in a manner known per se, by chemical means, i.e. with addition of dehydrating agents known per se. Depending on the nature of the reactants, the reaction conditions and the solvent employed, the cyclisation can, especially at elevated temperatures, also be carried out without adding a dehydrating agent, the water formed advantageously being removed azeotropically. However, in general the cyclisation is carried out at temperatures between about 40° and 120° C., preferably at 70°–90° C., in the presence of dehydrating agents and in the presence or absence of an aprotic organic solvent. Suitable dehydrating agents are, in particular, anhydrides of aliphatic monocarboxylic acids, having 2–5 C atoms, which are unsubstituted or substituted by halogen atoms or alkyl groups, such as acetic anhydride, propionic anhydride, butyric anhydride, valeric anhydride, trichloroacetic anhydride and trimethylacetic anhydride. The preferred dehydrating agent is acetic anhydride.

Compounds of the formula Ia or Ib, in which Z is —O—CO—CH=CH$_2$ or

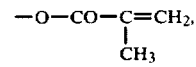

can also be obtained by reacting a compound of the formula Ia or IB, in which Z is —OH, with corresponding unsaturated acids, acid chlorides or esters. Finally, compounds of the formula Ia or Ib, in which Z is —COOCH=CH$_2$, can also be obtained by reacting compounds of the formula Ia or Ib, in which Z is —COOH, with corresponding alcohols or esters in the presence of acids or bases.

The starting materials of the formulae II to V are known or can be prepared by methods known per se. Compounds of the formula II can, for example, be obtained in a manner known per se, by reacting 3- or 4-nitrophthalic anhydride or the corresponding halogen compounds with amines HN-Y-Z' and then cyclising the resulting amidocarboxylic acids. The azidophthalic anhydrides of the formula IV are described in U.S. Pat. No. 3,002,003.

After the reaction has ended, the compounds of the formula Ia or Ib can be purified and isolated in the conventional manner, for example by concentrating the reaction solution or suspension in vacuo and washing the reaction product with water. The compounds of the formula Ia and Ib are in general obtained in the form of crystals.

The compounds of the formula Ib are valuable intermediates for the preparation of photo-crosslinkable polymers. Such polymers can be prepared by methods of synthesis, known per se, for the preparation of macromolecules having photoactive side groups. In principle, two methods can be employed:

1. Introduction of the azidophthalimidyl groups into an existing polymer chain containing corresponding functional groups, and
2. Synthesis of a polymer chain from monomers which already contain the photosensitive azidophthalimidyl group, the polymer chain being synthesisable by polymerisation or polyaddition.

Examples of suitable compounds for process (1) are those in the formula Ib in which Z is —OH, —COOH, —COCl, —NH$_2$ or —NH-alkyl having 1–4 C atoms, such compounds being reacted, for example, with polymers having recurring structural units of the formulae

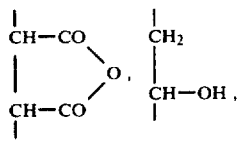

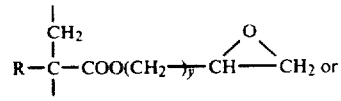

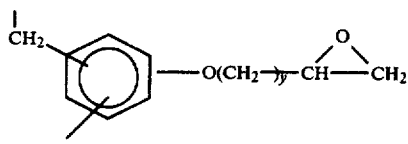

(where R is hydrogen or methyl and y is 1 or 2).

Suitable compounds for process (2) are, in particular, those of the formula Ib in which Z is —O—COCH=CH$_2$,

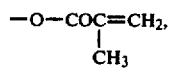

—COOCH=CH$_2$ or —OCH=CH$_2$, such compounds being polymerised, by themselves or together with other ethylenically unsaturated monomers, for example vinyl chloride, vinylidene chloride, acrylic acid, acrylonitrile, alkyl acrylates and alkyl methacrylates, styrene, ethylene, propylene, isoprene, chloroprene, 1,4-butadiene, vinyl acetate, vinyl propionate, maleic acid, fumaric acid or maleic anhydride.

The polymers thus obtained, having azidophthalimidyl side groups, can be photo-crosslinked, especially with UV light, and are suitable for photomechanical applications, for example for the manufacture of printing plates for the offset printing process, for the manufacture of photooffset lacquers, for unconventional photography, for example for the production of so-called vesicular images, or for colouring polymer images, which after exposure and development are not easily visible, by means of suitable dyes, for example oil-soluble dyes, or, if the polymer contains acid groups, for example carboxylic acid or sulphonic acid groups, with cationic dyes. The polymers according to the invention are used in particular as so-called photo-resists for the manufacture of printed circuits by methods known per se. In these, the side of the conductive plate provided with the photosensitive layer is exposed through a negative transparency carrying the conductor image and is then developed, after which the unexposed areas of the layer are removed with developer fluid. Exposure can be effected by means of sunlight, carbon arcs or xenon lamps, but is advantageously carried out with high pressure mercury lamps.

EXAMPLE 1

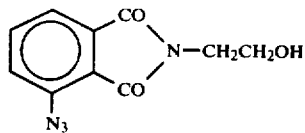

A mixture of 17.9 g (0.076 mol) of N-($\beta$-hydroxyethyl)-3-nitrophalimide and 5.11 g (0.078 mol) of sodium azide in 70 ml of dimethylsulphoxide is stirred at 50° C. for 12 hours. The solution is evaporated in vacuo and the residue is stirred with 200 ml of ice-water. The crystals which have precipitated are filtered off with suction, washed with 20 ml of water and dried for 24 hours at 80° C./100 mm Hg. 17 g (97% of theory) of N-($\beta$-hydroxyethyl)-3-azidophthalimide are obtained; melting point 141° C. (with decomposition). IR spectrum (CH$_2$Cl$_2$): 1775 cm$^{-1}$ and 1720 cm$^{-1}$ (CO—N—CO); 2120 cm$^{-1}$ (N$_3$).

N-($\beta$-Hydroxyethyl-3-nitrophthalimide, used in the above example, can be prepared as follows: a mixture of 19.3 g (0.1 mol) of 3-nitrophthalic anhydride, 6.7 g (0.1 mol) of ethanolamine, 50 ml of N,N-dimethylformamide (DMF) and 30 ml of toluene is boiled, the water formed in the course of the reaction being removed azeotropically. The reaction mixture is then evaporated to dryness. The residue is dissolved in 200 ml of methylene chloride and the solution is extracted by shaking with 100 ml of saturated sodium chloride solution. The methylene chloride solution is then dried with anhydrous sodium sulphate and evaporated. 18 g (76% of theory) of N-($\beta$-hydroxyethyl)-3-nitrophthalimide are obtained as an oily residue, which crystallises in a short time; melting point 93° C. IR spectrum (CH$_2$Cl$_2$): 1790 cm$^{-1}$ and 1730 cm$^{-1}$ (CO—N—CO); 1550 cm$^{-1}$ and 1370 cm$^{-1}$ (CO$_2$).

EXAMPLE 2

31.85 g (0.135 mol) of a mixture of N-($\beta$-hydroxyethyl)-3- and -4-nitrophthalimide are heated with 9.62 g (0.148 mol) of sodium azide in 360 ml of dimethylsulphoxide for 18 hours at 80° C. The solution is then concentrated in vacuo at 80° C. and the residue is stirred with 250 ml of water. The resulting suspension is filtered with suction, the filter residue is resuspended in 100 ml of water and this suspension is stirred for 18 hours. After filtering the suspension with suction, and drying the filter residue at 70° C./100 mm Hg, 24.5 g (78.6% of theory) of a mixture of N-($\beta$-hydroxyethyl)-3- and -4-azidophthalimide are obtained; melting point 102° C. (with decomposition). IR spectrum (CH$_2$Cl$_2$): 1785 cm$^{-1}$ and 1725 cm$^{-1}$ (CO-N-CO); 2125 cm$^{-1}$ (N$_3$).

The mixture of N-($\beta$-hydroxyethyl)-3- and -4-nitrophthalimide can be prepared as follows: 38.6 g (0.2 mol) of a mixture of 3- and 4-nitrophthalic anhydride, 13.4 g (0.22 mol) of ethanolamine, 100 ml of N,N-dimethylformamide and 60 ml of toluene are refluxed, the water formed in the course of the reaction being removed azeotropically. The reaction mixture is then evaporated to dryness in vacuo. The oily residue is dissolved in 200 ml of methylene chloride and the solution is twice extracted by shaking with saturated sodium chloride solution. The methylene chloride solution is dried with anhydrous sodium sulphate and evaporated to dryness. The oily residue crystallises on stirring with 500 ml of diethyl ether. After filtering the resulting yellow crystalline suspension with suction, and drying the filter residue at 40° C./100 mm Hg, 31.6 g (67% of theory) of a mixture of N-($\beta$-hydroxyethyl)-3- and -4-nitrophthalimide are obtained; melting point 80°–95° C. IR spectrum (dioxan): 1780 cm$^{-1}$ and 1720 cm$^{-1}$ (CO-N-CO); 1550 cm$^{-1}$ and 1340 cm$^{-1}$ (NO$_2$).

EXAMPLE 3

630 g (3.26 mols) of an isomer mixture of 3- and 4-nitrophthalic anhydride are dissolved in 1,632 mols of N,N-dimethylformamide, and 218 g (3.57 mols) of ethanolamine and 980 ml of toluene are added. The reaction mixture is refluxed, the water formed in the course of the reaction being distilled off azeotropically. The reaction mixture is then evaporated in vacuo at 90° C. 7,000 ml of dimethylsulphoxide and 263 g (4.04 mols) of sodium azide are added to the oily residue. The reaction mixture is then heated for 20 hours at 80° C., after which it is concentrated in vacuo at 90°-100° C., and the residue is stirred with 5,500 ml of water. The resulting yellow suspension is filtered with suction and the filter residue is dried in vacuo at 60° C. over solid sodium hydroxide. 647 g (85.5% of theory) of an isomer mixture of N-(β-hydroxyethyl)-3- and -4-nitrophthalimide are obtained; melting point 90°-105° C. (with decomposition). IR spectrum ($CH_2Cl_2$): 1780 cm$^{-1}$ and 1720 cm$^{-1}$ (CO—N—CO); 2125 cm$^{-1}$ ($N_3$).

EXAMPLE 4

A mixture of 2.9 g (0.01 mol) of 4-(3-nitrophthalimidyl)-cyclohexanol and 0.9 g (0.013 mol) of sodium azide in 20 ml of dimethylsulphoxide is stirred for 6 hours at 80° C. and then evaporated in vacuo at the same temperature. The residue is diluted with 20 ml of water. The product which has separated out is filtered off with suction, washed with 5 ml of water and dried for 24 hours at 80° C. in a drying cabinet. 2.6 g (91% of theory) of 4-(3-azidophthalimidyl)-cyclohexanol are obtained; melting point 155° C. (with decomposition). IR spectrum (KBr): 1775 cm$^{-1}$ and 1710 cm$^{-1}$ (CO—N—CO); 2130 cm$^{-1}$ ($N_3$).

The starting material used in the above example can be prepared as follows: A mixture of 29.4 g (0.25 mol) of 4-aminocyclohexanol, 43.9 g (0.227 mol) of 3-nitrophthalic anhydride, 120 ml of N,N-dimethylformamide and 75 ml of toluene is heated to the boil, with azeotropic removal of the water formed during the reaction, and is finally evaporated. The oily residue is dissolved in 1,000 ml of methylene chloride and the solution is extracted with four times 40.0 ml of 5% aqueous NaOH solution. The methylene chloride solution is dried with anhydrous sodium sulphate and evaporated. The oily residue is dissolved in 280 ml of hot methanol. On cooling, 16 g (22% of theory) of 4-(3-nitrophthalimidyl)-cyclohexanol crystallise out; melting point 215° C. IR spectrum ($CH_2Cl_2$): 1790 cm$^{-1}$ and 1730 cm$^{-1}$ (CO—N—CO); 1550 cm$^{-1}$ and 1370 cm$^{-1}$ ($NO_2$).

EXAMPLE 5

A mixture of 55 g (0.193 mol) of 4-(3-nitrophthalimidyl)-phenol and 13.8 g (0.212 mol) of sodium azide in 380 ml of dimethylsulphoxide is heated for 6 hours at 50° C. The reaction mixture is evaporated in vacuo at 80° C. and the residue is stirred with 1,000 ml of water for 18 hours. After filtering the resulting suspension, and drying the filter residue in a drying cabinet at 60° C. over phosphorus pentoxide, 56.6 g (95% of theory) of 4-(3-(azidophthalimidyl)-phenol are obtained; melting point 165° C. (with decomposition). IR spectrum (KBr): 1780 and 1715 cm$^{-1}$ (CO—N—CO); 2140 cm$^{-1}$ ($N_3$).

The starting material used in the above example can be prepared as follows: 34.3 g (0.31 mol) of 4-aminophenol and 59.9 g (0.31 mol) of 3-nitrophthalic anhydride in 600 ml of acetic acid are refluxed for 6 hours and the mixture is then stirred into 3,000 ml of water. The product which has precipitated is washed with water and dried for 24 hours at 70° C./30 mm Hg. 69 g (78% of theory) of 4-(3-nitrophthalimidyl)-phenol are obtained; melting point 202° C. IR spectrum (KBr): 1785 cm$^{-1}$ and 1725 cm$^{-1}$ (CO—N—CO); 1550 and 1350 cm$^{-1}$ ($NO_2$).

EXAMPLE 6

13.5 g (0.047 mol) of 4-(3-nitrophthalimidyl)aniline and 3.4 g (0.051 mol) of sodium azide in 120 ml of dimethylsulphoxide are heated for 18 hours at 80° C. The reaction mixture is then concentrated in vacuo at 80° C. and diluted with 100 ml of water, the mixture is filtered with suction and the filter residue is washed with 20 ml of water and dried for 24 hours in a drying cabinet at 80° C./100 mm Hg. 13.1 g (100% of theory) of 4-(3-azidophthalimidyl)-aniline are obtained; melting point 176° C. (with decomposition). IR spectrum (KBr): 1780 and 1725 cm$^{-1}$ (CO—N—CO); 2130 cm$^{-1}$ ($N_3$).

4-(3-Nitrophthalimidyl)-aniline, used in the above example, can be prepared as follows: 48.3 g (0.25 mol) of 3-nitrophthalic anhydride and 37.5 g (0.25 mol) of 4-aminoacetanilide in 500 ml of acetic acid are refluxed for 8 hours and are then cooled. The crystals which have separated out are filtered off with suction, washed with 150 ml of ethanol and dried for 24 hours at 80° C./30 mm Hg. 65 g (80% of theory) of 4-(3-nitrophthalimidyl)-acetanilide are obtained; melting point 255° C. 65 g (0.2 mol) of 4-(3-nitrophthalimidyl)-acetanilide are heated with a mixture of 400 ml of dioxan and 200 ml of concentrated hydrochloric acid for 3 hours at 90° C. and the whole is then left to stand for 24 hours at 25° C. The crystals which have separated out are filtered off with suction and washed with 100 ml of methanol. 45 g (70% of theory) of crude 4-(3-nitrophthalimidyl)-aniline hydrochloride are obtained. 45 g (0.14 mol) of this hydrochloride are mixed with 100 ml of water and 200 ml of a saturated sodium bicarbonate solution are added dropwise at 5° C. After one hour, the resulting fine precipitate is filtered off with suction, washed three times with 50 ml of water and dried for 24 hours at 25° C./1 mm Hg. 21 g (54% of theory) of 4-(3-nitrophthalimidyl)-aniline are obtained; melting point 177° C. IR spectrum (KBr): 1790 and 1725 cm$^{-1}$ (CO—N—CO); 1540 and 1360 cm$^{-1}$ ($NO_2$).

EXAMPLE 7

1.4 ml (0.01 mol) of triethylamine, followed by 0.72 g (0.011 mol) of sodium azide, are added to a mixture of 3.12 g (0.01 mol) of 4-(3-nitrophthalimidyl)-benzoic acid and 20 ml of dimethylsulphoxide. The reaction mixture is heated for 6 hours at 50° C. and is then evaporated in vacuo at 80° C.; the residue is stirred with 70 ml of water and the resulting solution is then brought to pH 1 with hydrochloric acid. The product which has precipitated is filtered off with suction, washed with 5 ml of methanol and dried for 24 hours in a drying cabinet at 80° C./100 mm Hg. 2.47 g (80% of theory) of 4-(3-azidophthalimidyl)-benzoic acid are obtained; melting point 300° C. (with decomposition). IR spectrum (KBr): 1790 and 1740 cm$^{-1}$ (CO—N—CO); 2150 cm$^{-1}$ ($N_3$).

The starting material used in the above example can be prepared as follows: 57.9 g (0.3 mol) of 3-nitrophthalic anhydride and 41.1 g (0.3 mol) of 4-aminobenzoic acid in 600 ml of acetic acid are refluxed for 6 hours and the mixture is then stirred into 1,000 ml of 50% aqueous ethanol. The yellow product which has precipitated is filtered off with suction, washed with water and dried at 80° C./30 mm Hg for 24 hours. 82 g (88% of theory) of 4-(3-nitrophthalimidyl)-benzoic acid are obtained; melting point >300° C. IR spectrum (KBr): 1790 and 1740 cm$^{-1}$ (CO—N—CO); 1550 and 1370 cm$^{-1}$ ($NO_2$).

EXAMPLE 8

2.58 ml (0.018 mol) of triethylamine, followed by 1.3 g (0.0198 mol) of sodium azide, are added to a mixture of 5.7 g (0.018 mol) of 6-(3-nitrophthalimidyl)-caproic acid in 35 ml of dimethylsulphoxide. The reaction mixture is heated for 6 hours at 50° C. and is then concentrated in vacuo, diluted with 100 ml of water and acidified with 4 ml of concentrated hydrochloric acid. The resulting suspension of the reaction product is stirred for 18 hours and filtered with suction, and the filter residue is washed with 20 ml of water and dried for 24 hours at 60° C./0.100. mm Hg, over phosphorus pentoxide. 5.1 g (94% of theory) of 6-(3-azidophthalimidyl)-caproic acid are obtained; melting point 87°–90° C. (with decomposition). IR spectrum ($CH_2Cl_2$): 1780 and 1725 $cm^{-1}$ (CO—N—CO); 2130 $cm^{-1}$ ($N_3$).

The starting material used in the above example can be prepared as follows: 3.86 g (0.02 mol) of 3-nitrophthalic anhydride and 2.9 g (0.022 mol) of 6-aminocaproic acid are heated under reflux for 8 hours and then evaporated. The solid residue is stirred with water, filtered off with suction and dried for 24 hours at 80° C. 5.7 g (93% of theory) of 6-(3-nitrophthalimidyl)-caproic acid are obtained; melting point 148°–150° C. IR spectrum ($CH_2Cl_2$): 1790 and 1725 $cm^{-1}$ (CO—N—CO); 1550 and 1370 $cm^{-1}$ ($NO_2$).

EXAMPLE 9

A solution of 3.78 g (0.02 mol) of 3-azidophthalic anhydride in 50 ml of dioxan is mixed with a solution of 2.74 g (0.02 mol) of p-aminobenzoic acid in 50 ml of dioxan and the mixture is left to stand for 3 hours. 5 ml of acetic anhydride are then added and the reaction mixture is heated for 1 hour at 85° C. After concentrating to dryness, the residue is mixed with water and the resulting crystals are filtered off with suction. 4.8 g (78% of theory) of 4-(3-azidophthalimidyl)-benzoic acid are obtained; melting point 300° C. (with decomposition).

EXAMPLE 10

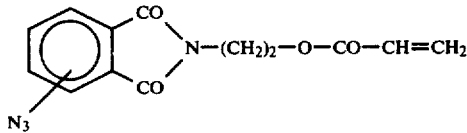

In a 500 ml sulphonation flask equipped with a 50 ml dropping funnel with pressure equaliser, a high-efficiency condenser with drying tube, and a thermometer, 23.1 g (0.1 mol) of the mixture of N-(β-hydroxyethyl)-3- and -4-azidophthalimide obtained according to Example 2 and 10.1 g (0.1 mol) of triethylamine (dried over NaOH) are dissolved in 250 ml of dry methylene chloride and the solution is cooled to 0° C., the operations being carried out under a nitrogen atmosphere. 9.05 g (0.1 mol) of acryloyl chloride are added dropwise to this solution at a rate such that the temperature does not exceed 10° C. After the reaction has ended, the reaction mixture is stirred until it has come to room temperature (20°–25° C.). The triethylamine hydrochloride which has precipitated during the reaction is separated from the remainder of the reaction solution by filtration. The methylene chloride extract is washed neutral with water, dried with Na sulphate and then concentrated in vacuo, without heating. 25.9 g (90.7% of theory) of a mixture of N-(β-acryloyloxyethyl)-3- and -4-azidophthalimide are obtained. NMR spectrum: $H_2C=CH-$ 5.7–6.3 (3H) ppm; (internal standard TMS=0).

EXAMPLE 11

In an apparatus of the type described in Example 10, 23.2 g (0.1 mol) of a mixture of N-(β-hydroxyethyl)-3- and -4-azidophthalimide and 10.1 g (0.1 mol) of triethylamine (dried over NaOH) are dissolved in 250 ml of dry methylene chloride and the solution is cooled to 0° C., the operations being carried out under a nitrogen atmosphere. 10.45 g (0.1 mol) of methacryloyl chloride are added dropwise to this solution at a rate such that the temperature does not exceed 10° C. After the reaction has ended, the reaction mixture is stirred until it has come to room temperature. The triethylamine hydrochloride which has precipitated during the reaction is separated from the remainder of the reaction solution by filtration. The methylene chloride extract is washed neutral with water, dried with Na sulphate and concentrated in vacuo, without heating. 27.65 g (92.2% of theory) of a mixture of N-(β-methacryloyloxyethyl)-3- and -4-azidophthalimide are obtained. NMR spectrum:

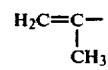

6.1 (1H) and 5.6 (1H) ppm; internal standard TMS=0.

EXAMPLE 12

15.0 g (0.05 mol) of the 6-(3-azidophthalimidyl)-caproic acid obtained according to Example 8 are dissolved in 327 g (2.75 mols) of thionyl chloride, and the solution is warmed to 80° C., the operations being carried out under yellow light. At 80° C., 0.5 ml of N,N-dimethylformamide is added to the clear solution obtained. The reaction mixture is stirred for 15 minutes at 80° C. and is then cooled to room temperature. This produces a beige-coloured suspension, which is filtered with suction, under $N_2$. The crude product is recrystallised from 250 ml of dry ligroin. 12.5 g (75.4% of theory) of 6-(3-azidophthalimidyl)-caproyl chloride are obtained; melting point 68°–69° C.

Elementary analysis:
  calculated: C 52.43%, H 4.09%, N 17.47%, Cl 11.06%,
  found: C 52.61%, H 4.13%, N 17.27%, Cl 9.04%.

EXAMPLE 13

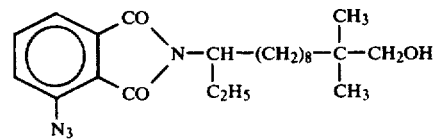

A mixture of 20.9 g (0.05 mol) of N-(1-ethyl-10,10-dimethyl-11-hydroxyundecyl)-3-nitrophthalimide and 3.55 g (0.055 mol) of sodium azide in 100 ml of dimethylsulphoxide is stirred for 24 hours at 80° C. The solution is evaporated in vacuo and the residue is diluted with 300 ml of water. The resulting emulsion is extracted with twice 100 ml of diethyl ether. The ether extracts are first dried with anhydrous sodium sulphate, and then evaporated. 14.7 g (71% of theory) of N-(1-ethyl-10,10-dimethyl-11-hydroxyundecyl)-3-azidophthalimide are obtained in the form of a viscous oil which cannot be distilled.

IR spectrum (CHCl₃): 1780 and 1725 cm⁻¹ (CO—N—CO); 2130 cm⁻¹ (N₃).

The starting material used in the above example can be prepared as follows: A mixture of 9.6 g (0.05 mol) of 3-nitrophthalic anhydride, 12.9 g (0.055 mol) of 1-ethyl-10,10-dimethyl-11-hydroxy-1-aminoundecane, 150 ml of toluene and 250 ml of dimethylformamide is heated to the boil, the water formed being removed azeotropically. The reaction mixture is then evaporated to dryness. The residue is dissolved in 150 ml of methylene chloride and the solution is extracted with three times 50 ml of 10% sodium carbonate solution. The methylene chloride solution is then dried over anhydrous sodium sulphate and evaporated. 20.9 g (about 100% of theory) of N-(1-ethyl-10,10-dimethyl-11-hydroxyundecyl)-3-nitrophthalimide are obtained in the form of a viscous oil which gradually crystallises after standing for several weeks; melting point 66°–68° C.

EXAMPLE 14

A mixture of 2.4 g (0.007 mol) of 1-(3-nitrophthalimidyl)-7-hydroxynaphthalene and 0.52 g (0.008 mol) of sodium azide in 14 ml of dimethylsulphoxide is stirred for 24 hours at 80° C. 100 ml of water are added to the solution. The crystals which have precipitated are filtered off with suction, washed with water and dried at 80° C./100 mm Hg. 1.7 g (73.6% of theory) of 1-(3-azidophthalimidyl)-7-hydroxynaphthalene are obtained; melting point 154° C. (with decomposition). IR spectrum (KBr): 1775 and 1720 cm⁻¹ (CO—N—CO); 2130 cm⁻¹ (N₃).

The starting material used in the above example can be prepared as follows: A mixture of 1.93 g (0.01 mol) of 3-nitrophthalic anhydride, 1.59 g (0.01 mol) of 1-amino-7-naphthol and 30 ml of acetic acid is refluxed for 17 hours. The resulting suspension is stirred with 300 ml of water, then filtered and the filter residue is then washed with water and dried. 2.9 g of crude product are obtained and are extracted with chloroform. The chloroform extract is stirred with 4 g of silica gel, filtered with suction whilst hot, and evaporated to dryness. 2.4 g (72% of theory) of 1-(3-nitrophthalimidyl)-7-hydroxynaphthalene are obtained; melting point 136°–7° C.

EXAMPLE 15

120.0 g of a mixture of N-(β-methacryloyloxyethyl)-3- and -4-azidophthalimide and 1.20 g of azoisobutyronitrile are dissolved in 545 ml of tetrahydrofuran, under yellow light, in a 1 liter reaction vessel equipped with a jacket, stirrer, high-efficiency condenser and thermometer. This solution is polymerised for 8 hours at 70° C., with stirring and under a nitrogen atmosphere. After the reaction has ended, the reaction mixture is cooled to room temperature (20°–25° C.) and the polymer is precipitated by dripping the reaction solution into 4 liters of n-hexane. 113.8 g (94.8% of theory) of a pale yellowish polymer are obtained; intrinsic viscosity η = 0.22 dl/g (c = 0.5% by weight in N,N-dimethylformamide at 25° C.).

To produce photosensitive plates, for example for the manufacture of printed circuits, a copper-laminated epoxy plate is coated with a 5% solution of the above polymer in N,N-dimethylformamide (DMF), using a production technique known per se [cf. Bogenschütz in "Fotolacktechnik" ("Photo-lacquer Technology"), Eugen G. Lenze-Verlag, DT 7968 Saulgau (1975)], in such a way that after drying at 40° C. a film about 5μ thick is formed. If this plate is now exposed to UV light (λ greater than 320 nm) through a line negative for one minute, the noncrosslinked parts then developed in tetrahydrofuran, and the unprotected copper surface etched away, the circuit corresponding to the line negative is obtained.

EXAMPLE 16

105.0 g of a mixture of N-(β-methacryloyloxyethyl)-3- and -4-azidophthalimide, 15.0 g of ethyl acrylate and 1.20 g of azoisobutyronitrile are dissolved in 545 ml of tetrahydrofuran, under yellow light, in an apparatus of the type described in Example 15. This solution is polymerised for 8 hours at 70° C., with stirring and under a nitrogen atmosphere. After the reaction has ended, the reaction mixture is cooled to room temperature and the polymer obtained is precipitated by dripping the reaction solution into 4 liters of n-hexane. 113.8 g (94.8% of theory) of a pale yellowish polymer are obtained; intrinsic viscosity η = 0.28 dl/g (c = 0.5% by weight in DMF at 25° C.).

EXAMPLE 17

2.5 g of N-(β-hydroxyethyl)-3-azidophthalimide, 5.0 g of a copolymer of methyl vinyl ether and maleic anhydride (GANTREZ 119; anhydride content 0.64 mol per 100 g Polymer; η = 5.76 cP; a commercial product from General Aniline + Film Corp.), i.e. a polymer having recurring structural units of the formula

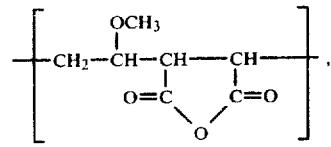

and 0.1 ml of concentrated sulphuric acid are dissolved in 77 ml of tetrahydrofuran in a 250 ml round-bottomed flask equipped with a high-efficiency condenser and a drying tube. After heating up the reaction mixture, the latter is kept under reflux for 48 hours, with stirring. When the reaction solution has cooled, the polymer obtained is precipitated by dripping the reaction solution into 500 ml of diethyl ether. 6.8 g (91% of theory) of a pale yellow polymer, containing 33.5% by weight of azide, are obtained.

EXAMPLE 18

2.5 g of N-(ω-carboxypentyl)-3-azidophthalimide, 2.5 g of a styrene/glycidyl methacrylate copolymer (molar ratio 1:1, molecular weight 25,000, i.e. a copolymer having recurring structural units of the formula

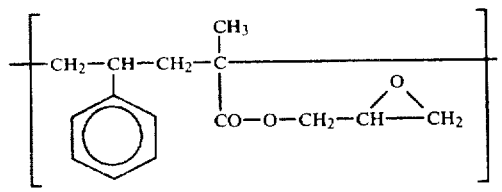

and 0.03 g of tetramethylammonium chloride are dissolved in 45 ml of cyclohexanone in an apparatus of the type described in Example 17. After heating up the reaction mixture, the latter is stirred for 1¾ hours at 110° C. After the mixture has cooled, the polymer is precipitated by dripping the reaction solution into 300 ml of n-hexane. 4.49 g (89.9% of theory) of a pale yellow polymer, containing 50% by weight of azide, are obtained.

EXAMPLE 19

0.7 g of N-(4-carboxyphenyl)-3-azidophthalimide, 1.4 g of a methyl methacrylate/glycidyl methacrylate copolymer having recurring structural units of the formula

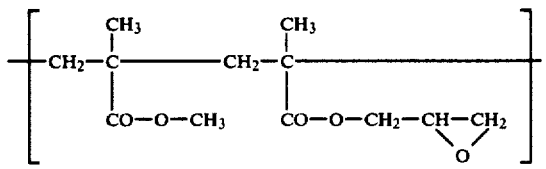

(molar ratio 1:1, molecular weight 25,000) and 0.005 g of tetramethylammonium chloride are dissolved in 25 ml of cyclohexanone in an apparatus of the type described in Example 17. After heating up, the reaction mixture is stirred for 2 hours at 110° C. The polymer is precipitated by dripping the reaction solution, when it has cooled, into 150 ml of n-hexane. 1.96 g (93.3% of theory) of a pale yellow polymer, containing 33.5% by weight of azide, are obtained.

EXAMPLE 20

Following a method analogous to that described in Examples 15 and 16, a mixture of N-(β-methacryloyloxyethyl)-3- and -4-azidophthalimide and acrylic acid, in a weight ratio of 1:4, is polymerised for 20 hours at 60° C. in the presence of 0.5% by weight of azoisobutyronitrile, based on the weight of the monomers. The polymer obtained is precipitated by dripping the reaction solution into diethyl ether. A pale yellowish polymer is obtained; intrinsic viscosity η=0.23 dl/g (c=0.5% by weight in DMF at 25° C.).

The polymers obtained according to Examples 16–20 can be used for the manufacture of printed circuits by the method described.

EXAMPLE 21

The polymer obtained according to Example 20 is tested in a photographic layer material. First a coating solution of the following composition is prepared:

| gelatin | 2 g/m² |
|---|---|
| polymer according to Example 20 | 1 g/m² |
| wetting agent (polyethylene oxide stearate) | 20% by weight, based on the weight of the polymer |
| photosensitiser (2-p-methoxy-benzyl-6'- and -7'-sulphoquin-oxaline) | 4% by weight, based on the weight of the polymer |
| hardener (2-hydroxy-6-amino-s-triazine-4-N-methylmorpholinium tetrafluoborate) | 8% by weight, based on the weight of the gelatin |

This coating solution is coated onto a transparent carrier, i.e. a polyester film. After the gelatin has hardened, the film is exposed through a screen negative (step wedge with 12 steps) for 15 seconds, using a 400 watt high pressure lamp. The unexposed portions are washed out in water at 20° C. in the course of 20 seconds. The crosslinked polymer is dyed, or rendered visible, with a cationic dye, for example the dye of the formula

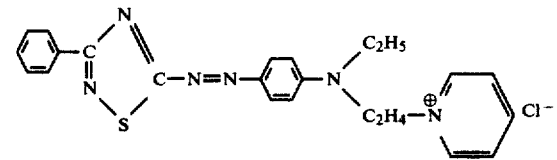

used as an aqueous solution; all 12 steps of the step wedge are reproduced.

EXAMPLE 22

10.42 g (0.035 mol) of N-(β-methacryloyloxyethyl)-3-azidophthalimide and 2.32 g (0.023 mol) of ethyl acrylate are dissolved in 50 ml of tetrahydrofuran and the solution is warmed to 70° C. under nitrogen, the operations being carried out under yellow light. 0.127 g of azoisobutyronitrile is dissolved in 7 ml of tetrahydrofuran and introduced into the monomer solution from a dropping funnel flushed with nitrogen. The reaction mixture is stirred for a further 7 hours at 70° C. and is then cooled to room temperature, filtered and precipitated in 1 liter of diethyl ether. The pale yellowish suspension is filtered with suction, and the product obtained is dried in vacuo at 30° C. Yield: 11.85 g=93% of theory; 11.8% by weight N; intrinsic viscosity η0.18 dl/g (c=0.5% by weight in DMF at 25° C.).

A copper-coated plate (about 5×10 cm) is coated on a commercial centrifuge with a 10% solution of the above polymer in DMF (viscosity about 1 Pa.s). The copper plate provided with the photolacquer is then dried in a circulating air oven at 60° C. Thereafter the coated plate is exposed for various periods of time, through a 21 step film negative original (a so-called "21-step sensitivity guide"), to a 400 watt mercury high-pressure lamp in front of which is a Pyrex glass filter, the distance from lamp to plate being 60 cm. The exposed plate is developed in 1,1,1-trichloroethane and etched in FeCl₃ solution. To determine the photosensitivity, the last step of the original visible after etching is recorded in each case.

| Exposure time | Step |
|---|---|
| 1 minute | 0 |
| 3 minutes | 0–1 |
| 6 minutes | 4 |

Comparative example: Using the method described in Example 15, N-(β-hydroxyethyl)-3-azidophthalimide is reacted with a maleic anhydride polymer ("Gantrez AN", a commercial product from GAF) to give a polymer having recurring structural units of the formula

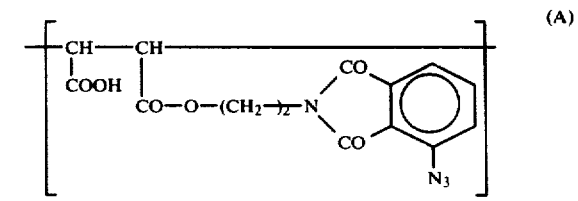

(A)

The same maleic anhydride polymer is reacted analogously with mono-β-hydroxyethyl 3-azidophthalate to give a polymer having recurring structural units of the formula

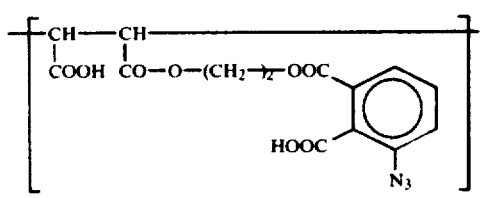

(B).

If polymers (A) and (B) are irradiated with UV light of wavelengths greater than 320 nm, polymer (A) exhibits a photosensitivity which is 5–10 times higher than that of polymer (B).

What is claimed is:

1. A compound of formula Ib

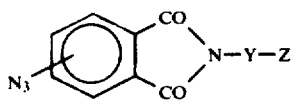

(Ib)

in which Y is alkylene having 2 to 18 carbon atoms; said alkylene substituted by one or two phenyl groups, by one or two cycloalkyl groups having 5 to 8 carbon atoms or by one or two aralkyl groups having 7 or 8 carbon atoms; phenylene, naphthylene, biphenylene, cyclohexylene, dicyclohexylmethane or

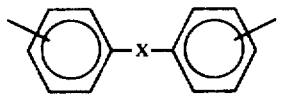

where X is

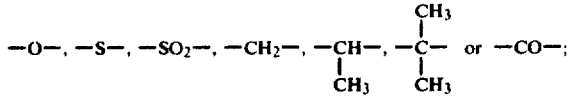

or said phenylene, said naphthylene, said diphenylene, said cyclohexylene, said dicyclohexylmethane or said

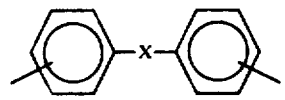

substituted, per ring, by one halogen atom, by one alkyl group having 1 to 4 carbon atoms, by one cycloalkyl group having 5 to 7 carbon atoms or by one aralkyl group having 7 or 8 carbon atoms, and Z is —OH.

2. A compound of the formula Ib according to claim 1, in which the $N_3$ group is joined to the benzene ring in the ortho-position to a carbonyl group.

3. A compound of the formula Ib according to claim 1, in which Y is unsubstituted alkylene having 2–18 C atoms, cyclohexylene, naphthylene or phenylene and Z is —OH.

4. A compound according to claim 1, of the formula VII

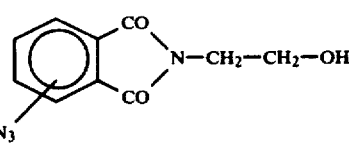

(VII).

5. A compound according to claim 4 which is N-(β-hydroxyethyl)-3-azidophthalimide.

* * * * *